US007800068B2

(12) United States Patent
Vugts et al.

(10) Patent No.: US 7,800,068 B2
(45) Date of Patent: Sep. 21, 2010

(54) CONVEYOR SYSTEM

(75) Inventors: Jan Vugts, Gravenmoer (NL); Jozef Antonius Willem Maria Corver, Nuenen (NL)

(73) Assignee: IMA Life S.R. L., Dell'Emilia (IT)

( * ) Notice: Subject to any disclaimer, the term of this patent is extended or adjusted under 35 U.S.C. 154(b) by 66 days.

(21) Appl. No.: 11/885,292

(22) PCT Filed: Feb. 22, 2006

(86) PCT No.: PCT/GB2006/000628

§ 371 (c)(1),
(2), (4) Date: Jul. 9, 2008

(87) PCT Pub. No.: WO2006/092557

PCT Pub. Date: Sep. 8, 2006

(65) Prior Publication Data

US 2009/0153838 A1 Jun. 18, 2009

(30) Foreign Application Priority Data

Mar. 2, 2005 (GB) ................................ 0504284.1

(51) Int. Cl.
*G01J 5/02* (2006.01)

(52) U.S. Cl. ................................................. 250/341.1

(58) Field of Classification Search ............... 250/341.1; 356/51, 427, 433, 448; 700/109, 110
See application file for complete search history.

(56) References Cited

U.S. PATENT DOCUMENTS

| 5,523,560 A | * | 6/1996 | Manique et al. | 250/223 B |
| 2004/0065832 A1 | * | 4/2004 | Cluff et al. | 250/341.1 |
| 2006/0017916 A1 | * | 1/2006 | Clarke et al. | 356/300 |

FOREIGN PATENT DOCUMENTS

| WO | WO 2004/063726 | 7/2004 |
| WO | WO 2005/119214 | 12/2005 |

* cited by examiner

*Primary Examiner*—David P Porta
*Assistant Examiner*—Marcus H Taningco
(74) *Attorney, Agent, or Firm*—Knobbe Martens Olson & Bear LLP

(57) ABSTRACT

A conveyor system comprises means for conveying a sample at a controlled velocity between functions of a production line and through an interrogation zone, means for generating at least one beam of electromagnetic radiation of a terahertz frequency and directing the beam through the interrogation zone, means for detecting the electromagnetic radiation reflected from or transmitted through the sample as it moves through the interrogation zone, and means for analyzing the detected electromagnetic and for outputting a signal to at least one of the functions in dependence on the result of the analysis.

25 Claims, 3 Drawing Sheets

CONVEYOR SYSTEM

The present invention relates to a conveyor system, and in particular to a method of, and apparatus for, inspecting a sample conveyed on a conveyor system, for example, between functions of a production line.

In-line filling machines for dispensing products, such as liquid and/or powder drug samples, into containers or vials typically include a conveyor system for conveying the containers between functions. A filling station receives empty vials from the conveyor system, sequentially fills the vials with an accurate amount of one or more products and closes the thus-filled vials with closure members, for example, stoppers. The conveyor system then conveys the closed vials to an inspection station which checks that the vials have been correctly filled. A reject station is provided downstream from the inspection station for removing incorrectly filled vials from the production line. A sealing station may also be provided downstream from the reject station for sealing the vials.

International Patent Application WO 99/67606 describes an inspection station that checks the weight of vials on a production line using NMR techniques. The inspection station includes a magnet for creating a static magnetic field over an interrogation zone to produce a net magnetization within a vial located in the interrogation zone, and an RF coil for applying an alternating magnetic field over the interrogation zone to cause pulse excitation of the sample contained within the vial. After the excitation, the sample relaxes and emit electromagnetic energy at the Larmor frequency of the molecules of the sample, the magnetic component of which induces a signal, known as the free induction decay (FID), in the form of current in the RF coil. The amplitude of the induced current varies, inter alia, with the number of molecules in the sample. The amplitude of the induced current can be compared to that produced by a calibration sample with known mass to determine the mass of the sample under analysis.

If more than one vial is located within the interrogation zone, the additional vial or vials will also develop their own net magnetization, and emit their own FIDs induced in the RF coil, producing an interference, or "cross coupling" effect on the FID induced in the RF coil. In order to eliminate the cross coupling effects of neighboring vials on the NMR measurement of the mass of the contents of the vial, the spacing of vials on the conveyor system is controlled so that only one vial is located within the interrogation zone at a time. This has the effect of limiting the rate at which vials are conveyed on the production line to around 600 vials per minute.

There are number of other disadvantages associated with the use of such an inspection system:
  it is not possible to determine the distribution of the moisture;
  the equipment is relatively expensive; and
  the equipment requires careful calibration, which is relatively complex and can take quite a long time to complete.

It is an aim of at least the preferred embodiment of the invention to provide an alternative method of inspecting a moving sample.

In a first aspect, the present invention provides a method of quality control on a production line in which samples are conveyed between functions of the production line, the method comprising the steps of conveying each sample at a controlled velocity through an interrogation zone, generating at least one beam of electromagnetic radiation of a terahertz frequency and directing the beam through the interrogation zone, detecting the electromagnetic radiation reflected from or transmitted through a sample as it moves through the interrogation zone, analyzing the detected electromagnetic radiation, and outputting a signal to at least one of the functions in dependence on the result of the analysis.

The electromagnetic radiation of a terahertz frequency typically has a frequency within the range from 100 GHz ($10^{11}$ Hz) to 30 THz ($3 \times 10^{13}$ Hz). Through distinctive absorption and/or reflection of terahertz radiation by different material, physical and/or chemical characteristics of the sample can be determined, such as, but not limited to:
  "Fingerprinting" or characterization of the sample;
  Sample density;
  Location and size of water concentrations;
  Presence of metallic particles;
  Sample temperature;
  Homogeneity of suspensions; and
  Discontinuities in the sample packaging or container.

By detecting the radiation reflected from or transmitted through the sample as it passes through the interrogation zone, time domain waveforms can be obtained from each part of the sample. These waveforms can then be used to provide information about the sample under analysis. For example, information regarding density of a sample contained within a glass or plastics container can be obtained from reflected terahertz radiation. Whilst glass and plastics is substantially transparent to terahertz radiation, due to the difference in refractive index between the material of the container and the material of the sample, the interfaces between the container and the sample will at least partially reflect terahertz radiation. By monitoring the time difference between the radiation reflected from the container/sample and the sample/container interfaces as the sample passes through the interrogation zone, an indication of the density of the sample and the homogeneity of the sample density can be obtained. As another example, a change of shape and/or attenuation of the terahertz radiation as it passes through the interrogation zone can be indicative of the material of the sample. Any imperfections in the surface of the container, in particular a plastics container, can be detected from the angle at which the beam is reflected from the interface.

Furthermore, as the radiation passes through the sample, different materials or structures within the sample will reflect the radiation in turn. These reflections will reach the detector at different times, and with different characteristics depending on the nature of the feature within the sample causing the reflection. By recording the reflections received from each point at which the beam is incident upon the sample as it moves through the interrogation zone, information regarding the contents of the sample can be obtained.

The time domain waveforms may be transformed using a Fourier transformation algorithm into frequency domain waveforms from which physical and/or chemical characteristics of the sample may be determined. Certain materials can be analyzed through frequency-dependent absorption, dispersion, and reflection of terahertz signals passing through a sample. By generating pulses of electromagnetic radiation having different frequency components within the terahertz range, and monitoring changes in the amplitude and/or phase of the components of the radiation as the sample passes through the interrogation zone, it is possible to distinguish between different materials within the sample. For example, water molecules have a characteristic absorption of terahertz radiation, and so the inspection technique can be used to determine the location and the shape of volumes with a high concentration of water molecules within the sample.

Due to the speed at which a sample can be analyzed using a terahertz inspection technique, such a technique may be used to perform quality control over a batch of moving samples on a production line. As, unlike an NMR inspection system, there are no issues regarding cross-coupling, the rate at which samples are conveyed on the production line can be increased to around 1000 to 1200 samples per minute by reducing the spacing between the samples, in comparison to the practical limit of around 600 samples per minute when an NMR inspection system is used. This can enable sample throughput to be increased without having to increase the velocity at which the samples are conveyed. Pharmaceutical containers such as vials and ampoules tend to have relatively high height to diameter ratios, which makes them susceptible to toppling as they are conveyed through a conveying system. By arranging the samples on the conveyor such that adjacent samples (or containers in which the samples are located) are touching, this can reduce the likelihood of samples falling as they are conveyed. A row of closely packed containers can be transferred to the conveyor directly from a freeze dryer, or from a buffer for receiving the containers from the freeze dryer or filling station as appropriate.

The detected radiation may be compared with that reflected from or transmitted through a reference sample conveyed through the interrogation zone at the controlled velocity, for example through obtaining time domain waveforms and/or frequency domain waveforms from the detected radiation and comparing those waveforms with the equivalent waveforms generated from the reference sample. In this case, there may be no specific requirement to determine one or more physical and/or chemical characteristics of the sample. For example, if from the result of the comparison it is determined that the sample is substantially the same as the reference sample, or differs from the reference sample in a non-critical manner, then the sample is not rejected. Otherwise, a signal may be sent to a rejection station to indicate that the sample is to be rejected. As an alternative, the sample may be rejected only if specific physical and/or chemical features of the sample are identified and which are not present within the reference sample, for example metallic particles. Therefore, in a second aspect the present invention provides a Thus, in a second aspect the present invention provides a method of quality control on a production line in which samples are conveyed between stations of the production line, the method comprising the steps of conveying each sample at a controlled velocity through an interrogation zone, generating at least one beam of electromagnetic radiation of a terahertz frequency and directing the beam through the interrogation zone, detecting the electromagnetic radiation reflected from or transmitted through a sample as it moves through the interrogation zone, analyzing the detected electromagnetic radiation, and rejecting the sample in dependence on the result of the analysis.

In addition to, as or as an alternative to, outputting a signal to a rejection station, a signal may be output to a filling station for filling containers with the samples. The result of the comparison may be indicative of, for example, too much filler, insufficient mixing of the samples, inhomogeneity of the samples, or other fault of the filling station, and this fault may be rectified, or at least ameliorated, by the filling station in dependence on information contained within the signal.

The container may be formed from any suitable material, although preferred materials are plastics and glass, such as quartz, materials that are substantially transparent to the beam of electromagnetic radiation. Pharmaceutical vials typically include stoppers for sealing the container, and these stoppers are also preferably formed from material that is substantially transparent to the beam of electromagnetic radiation.

The interrogation zone is preferably a two-dimensional zone that may extend substantially orthogonally to the direction of movement of the sample therethrough. To irradiate the interrogation zone with electromagnetic radiation, a single beam of electromagnetic radiation may be scanned across the interrogation zone. For example, the beam of electromagnetic radiation may be incident on a rotating multi-faceted reflector or crystal that optically scans the incident beam across the interrogation zone. Using this technique, the beam of electromagnetic radiation would be incident upon "slices" of a sample passing through the interrogation zone, the spacing between the slices being dependent upon the speed of rotation of the crystal and the speed at which the sample passes through the interrogation zone. Alternatively, a plurality of substantially parallel beams of electromagnetic radiation may be directed through the interrogation zone. These beams may be generated from a single radiation source located at or near the focus of a concave reflecting surface or mirror upon which the beams are incident and reflected towards the interrogation zone as a substantially parallel set of beams. Using this technique, the beams can be incident upon substantially the entire sample as it passes through the interrogation zone.

In a third aspect, the present invention provides a conveyor system comprising means for conveying a sample at a controlled velocity between functions of a production line and through an interrogation zone, means for generating at least one beam of electromagnetic radiation of a terahertz frequency and directing the beam through the interrogation zone, means for detecting the electromagnetic radiation reflected from or transmitted through the sample as it moves through the interrogation zone, and means for analyzing the detected electromagnetic and for outputting a signal to at least one of the functions in dependence on the result of the analysis.

In a fourth aspect, the present invention provides a conveyor system comprising means for conveying a sample at a controlled velocity through an interrogation zone, means for generating at least one beam of electromagnetic radiation of a terahertz frequency and directing the beam through the interrogation zone, means for detecting the electromagnetic radiation reflected from or transmitted through the sample as it moves through the interrogation zone, means for analyzing the detected electromagnetic, and means for rejecting the sample in dependence on the result of the analysis.

In addition to pharmaceuticals, such method or conveyor system can be used in a variety of applications, including but not limited to cosmetics, perfumes, industrial chemicals, biological samples and food products.

Features described above in relation to first and second aspects of the invention are equally applicable to the third and fourth aspects of the invention, and vice versa.

Preferred features of the present invention will now be described with reference to the accompanying drawing, in which.

Figure 1:
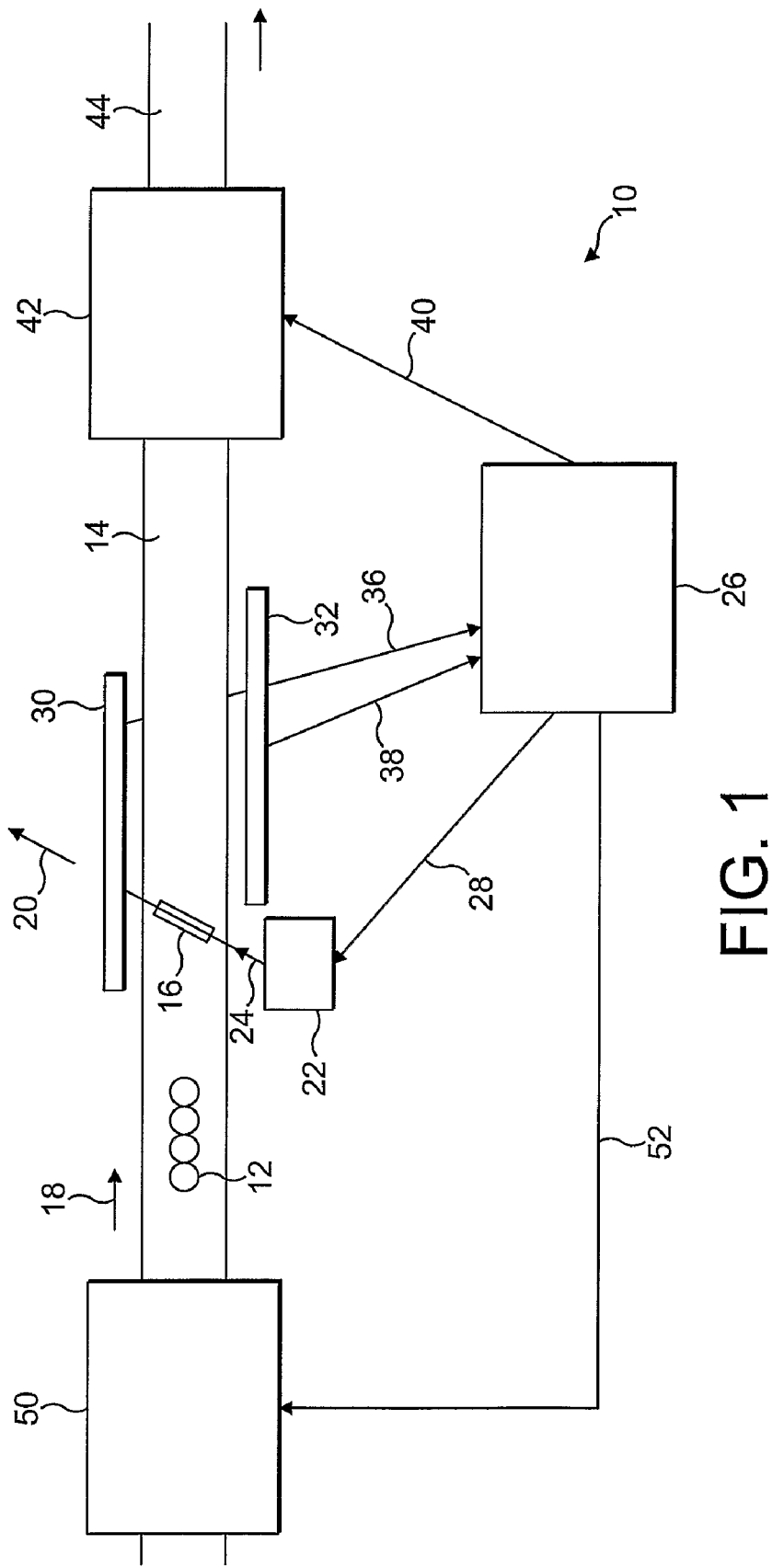
FIG. 1 illustrates schematically a plan view of a conveyor system for conveying samples between functions.

FIG. 1 illustrates schematically a conveyor system 10. In the preferred embodiment, the conveyor system is used to convey sterile pharmaceutical glass or plastics vials 12 containing a pharmaceutical sample between functions, for example, between a freeze dryer and a capping station, or may be part of an in-line filling system for conveying containers between a filling station and a capping station, or, as illustrated, between a filling station 50 and a reject station 42. However, the conveyor system may be configured to convey containers other than vials, such as blister packs, ampoules and syringes.

A conveyer belt 14 conveys the vials at a controlled speed, typically a constant speed, through the system 10. The conveyor belt 14 generally comprises an endless chain driven by motor-driven gear wheels, and may be constructed from materials selected from a group including Kevlar®, Teflon®, polyester, polyurethane, aramide, glass, or other thermoplastic materials. As ampoules and syringes are highly mechanically unstable, the conveyer belt 14 may be adapted to hold such containers while being transported through the system 10. A row of vials 12 may be conveyed to the conveyor belt 14 using a star wheel system so that the vials 12 have a regular pitch, for example between 40 and 80 mm. Alternatively, and as illustrated, the vials 12 may be conveyed to the conveyor belt 14 from, for example a buffer system or directly from a shelf of a freeze dryer, so that adjacent vials are in contact.

Figure 2:
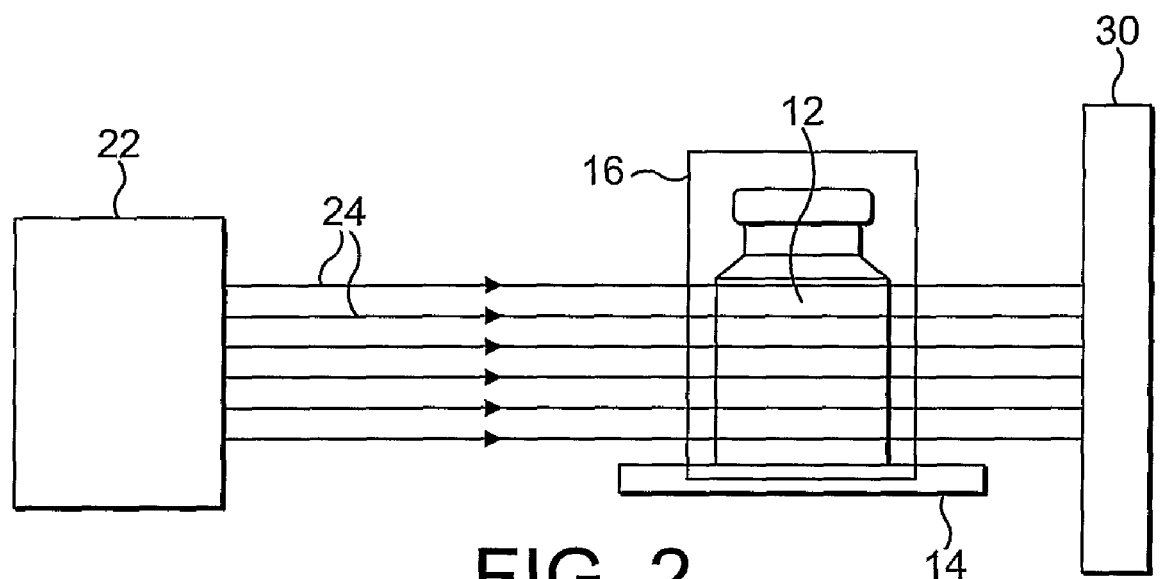
FIG. 2 illustrates schematically one arrangement for illuminating the interrogation zone of the system of FIG. 1.
Figure 3:
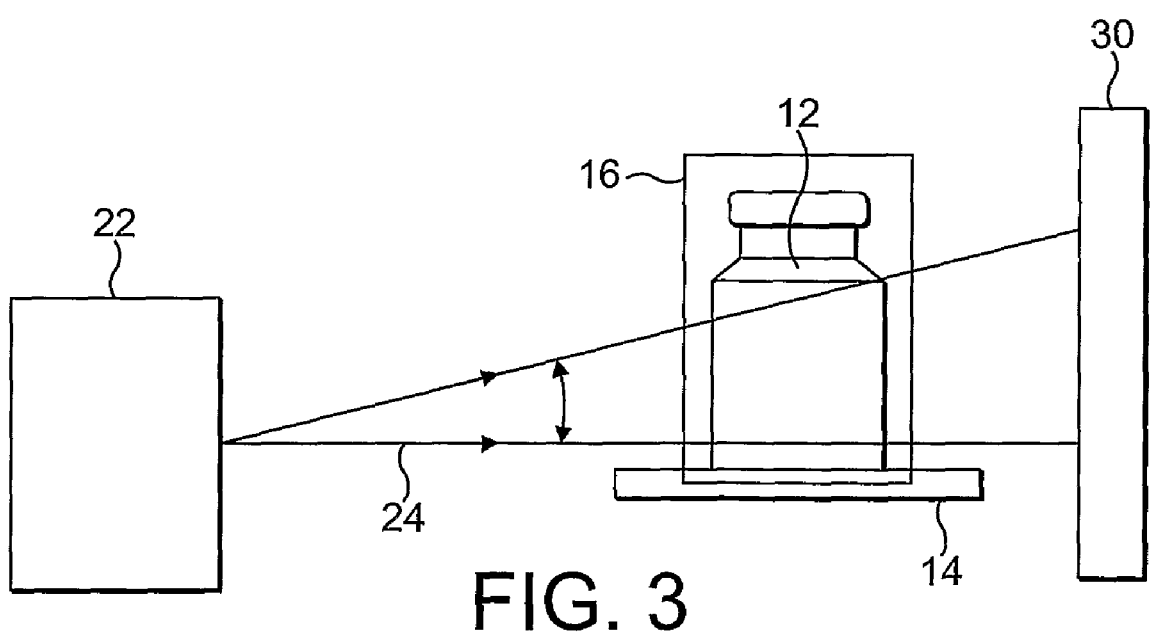
FIG. 3 illustrates schematically another arrangement for illuminating the interrogation zone of the system of FIG. 1.

As illustrated in FIGS. 2 and 3, the conveyor belt 14 conveys the vials through an interrogation zone 16. As illustrated in those figures, the interrogation zone 16 is a region that extends obliquely relative to the direction of motion of the vials 12 on the conveyor belt 14, as indicated at 18 on FIG. 1, and is preferably larger than the cross-section of the vials 12 in the oblique direction 20 also indicated in FIG. 1.

The interrogation zone 16 is at least partially illuminated with electromagnetic radiation of a terahertz frequency (or "terahertz radiation"), that is, electromagnetic radiation having a frequency within the range from 100 GHz ($10^{11}$ Hz) to 30 THz ($3 \times 10^{13}$ Hz). The detection of the contents of a sample using terahertz radiation is known, for example, GB 2,399, 626 and U.S. Pat. No. 5,710,430, the contents of which are incorporated herein by reference. In overview, in the arrangement illustrated in FIG. 2 a generator and transmitter system 22 generates a plurality of substantially parallel beams 24 of pulsed terahertz radiation and directs the beams 24 across the interrogation zone 16. These pulses may be generated by any suitable technique. One technique that may be used to generate these pulses of terahertz radiation is to use a diode pumped solid state laser to optically pump a Ti:sapphire laser. This laser produces light pulses at a wavelength of 780 nm. One of these pulses impinges on an InGaAs semiconductor sample to create electron-hole pairs, which are coherently accelerated in the depletion layer of the semiconductor, acting as dipoles that emit short pulses of terahertz radiation. The terahertz radiation generated in this manner has an extremely broad bandwidth, generally extending over the aforementioned frequency range. As another alternative, a free electron laser may be used to generate intense, coherent, and tunable terahertz radiation.

In order to generate a parallel set of beams from divergent beams emitted from a single source, the beams may be incident upon one or more concave mirrors, which direct the beams towards the interrogation zone 16 as a substantially parallel set of beams 24. Alternatively, a plurality of sources may be used, each of which generates a respective beam of terahertz radiation, which is transmitted towards the interrogation zone 16. In the arrangement illustrated in FIG. 3, a single beam of terahertz radiation 24 is scanned across the interrogation zone 16, for example by directing the beam on to a rotating, multi-faceted crystal or other reflector which reflects the beam at a varying angle of reflection towards the interrogation zone 16. Returning to FIG. 1, a control system 26 generates control signals 28 for controlling the generator and transmitter system 22.

Figure 4:
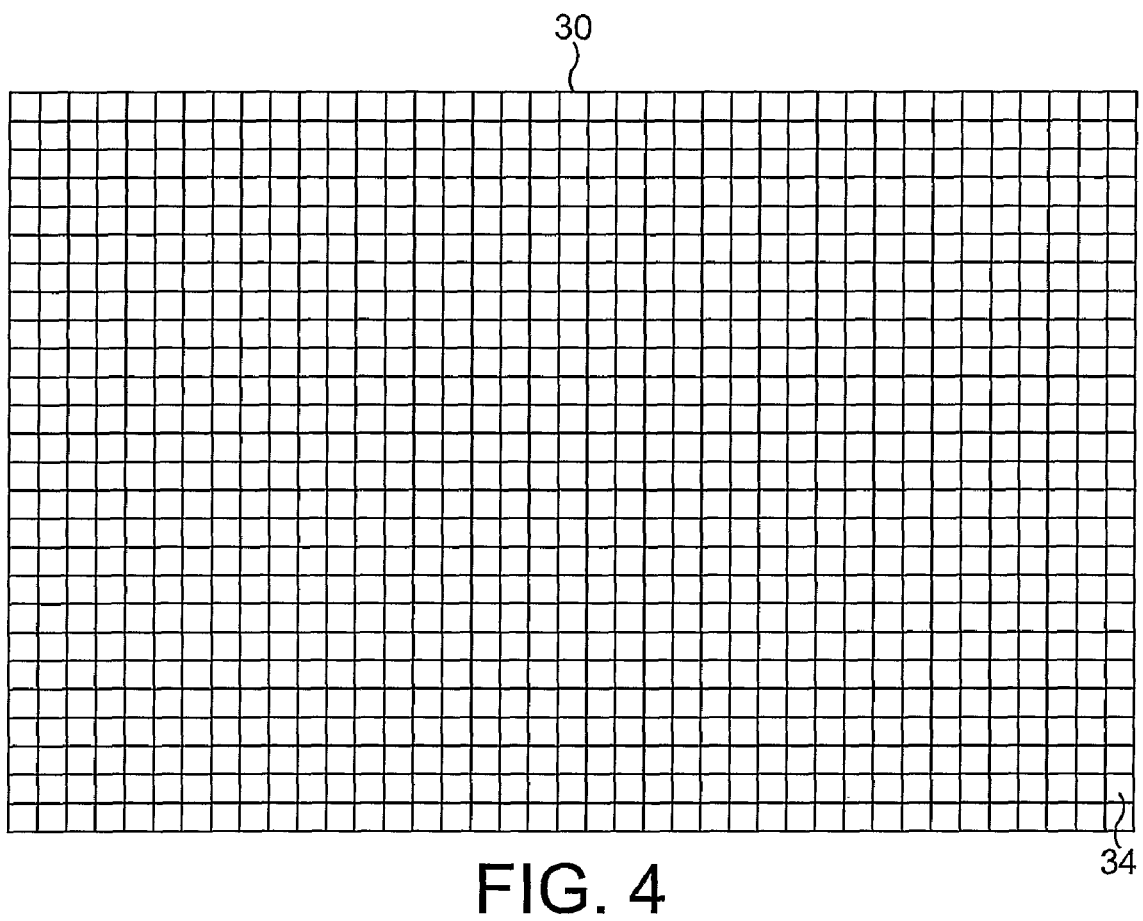
FIG. 4 illustrates schematically one of the detectors of the system of FIG. 1.

In the example illustrated in FIG. 1, two terahertz radiation detector arrangements 30, 32 are provided for detecting the terahertz radiation transmitted through and reflected from a vial 12 as it passes through the interrogation zone 16, respectively. However, depending on the characteristics of the sample that are of interest, only one of these two detector arrangements 30, 32 may be provided. As illustrated in FIG. 4, each detector arrangement 30, 32 may comprises an array of individual detectors 34 each for detecting terahertz radiation incident thereon. The imaging array may be provided by any suitable array of detectors, for example the detectors manufactured by Picometrix Inc., in which a microfabricated antenna structure is deposited over a fast photoconductive material, such as GaAs. The antenna structure serves to concentrate the incident radiation upon the surface of the GaAs layer, which creates a photocurrent within the detector 34. Signals 36, 38 indicative of the amplitude and phase of the photocurrent generated within each detector arrangement 30, 32 respectively are output to the control system 26.

In use, as a glass or plastics vial 12 is conveyed through the interrogation zone 16, it is illuminated by at least one beam 24 of terahertz radiation. As the material from which the vial 12 is formed is substantially transparent to terahertz radiation, the terahertz radiation detected by the detecting arrangements 30, 32 as the vial passes through the interrogation zone 16 can provide information regarding the pharmaceutical sample contained within the vial 12.

For instance, through distinctive absorption and/or reflection of terahertz radiation by different materials, physical and/or chemical characteristics of the pharmaceutical sample can be determined. From the signals received from the detector arrangements 30, 32 when one or more broadband beams of terahertz radiation passes through the interrogation zone 32, information regarding, for example, the presence and size of metallic particles and water concentrations, and homogeneity of suspensions can be obtained. When using a terahertz beam of a single frequency, information regarding the sample density can be obtained through measurement of the time of flight of the beam through the sample.

Depending on the outcome of this analysis of the received signals 36, 38 by the control system 26, the control system 26 may determine that one of the vials 12 should be rejected from the stream of vials conveyed by the system 10, for example due to the presence of one or more metallic particles. In this event, the control system 26 outputs a signal 40 to a reject station 42 provided downstream from the interrogation zone that a particular vial 12 is to be rejected. Depending on the ease at which a rejected vial 12 can be separated from the other vials on the conveyor belt 14, for example, depending on the spacing between adjacent vials, the reject station 42 can direct rejected vials to a reject buffer (not shown), and direct the non-rejected vials to an out-feed section 44 of the conveyor system 10. Alternatively, where the vials are more closely spaced, or touching, the reject station 42 may be configured to mark, either visibly or invisibly (for example magnetically), the rejected vial for subsequent rejection in the out-feed section 44 of the conveyor system 10.

As an alternative to performing a full analysis of the physical and/or chemical characteristics of the sample contained within the vial 12, the control system 26 may be configured to compare the signals 36, 38 received from the vial 12 as it passes through the interrogation zone with equivalent signals received when a vial containing a reference sample of known physical and chemical character was previously conveyed through the interrogation zone 16 at the controlled velocity.

If from the result of the comparison it is determined that the sample is substantially the same as the reference sample, or differs from the reference sample in a non-critical manner, then the sample is not rejected. Otherwise, a signal 40 may be sent to the reject station 42 indicating that the vial 12 is to be rejected.

As an alternative to, or in addition to, outputting a signal 40 to the reject station 42 indicating that the vial 12 is to be rejected, a signal 52 may be sent to the filling station 50 to advise the filling station 50 of an incorrect filling of a vial 12, for example due to insufficient filling or overfilling of the vial 12, or insufficient mixing of the sample. Action may then be taken automatically by the filling station 50, or by an operator of the filling station 50, in dependence on the cause for the incorrect filling.

The invention claimed is:

1. A method of quality control on a production line in which samples comprising containers containing products are conveyed between functions of the production line, the method comprising:
    filling the containers at a filling station with products;
    conveying each sample at a controlled velocity from the filling station through an interrogation zone;
    generating at least one beam of electromagnetic radiation of a terahertz frequency;
    directing the beam to the interrogation zone;
    detecting the electromagnetic radiation reflected from or transmitted through a sample as it moves through the interrogation zone;
    analyzing the detected electromagnetic radiation at least to determine physical or chemical characteristics of the products within the containers; and
    outputting a signal to at least the filling station, wherein the signal corresponds to a result of analyzing the detected electromagnetic radiation.

2. The method according to claim 1, wherein at least one time domain waveform is obtained from the detected radiation, the time domain waveform being used to determine said one or more physical and/or chemical characteristics of the products within the containers.

3. The method according to claim 2, wherein said at least one time domain waveform is used to generate at least one frequency domain waveform from which said one or more physical and/or chemical characteristics of the products within the containers.

4. The method according to claim 1, wherein adjacent containers are touching.

5. The method according to claim 1, wherein the container is formed from glass or plastics material.

6. The method according to claim 1, wherein the beam of electromagnetic radiation is incident on a rotating multi-faceted reflector that optically scans the incident beam across the interrogation zone.

7. The method according to claim 1, wherein a plurality of substantially parallel beams of electromagnetic radiation are directed through the interrogation zone.

8. The method according claim 1, wherein the interrogation zone extends substantially orthogonally to the direction of movement of the sample therethrough.

9. The method according to claim 1, wherein the interrogation zone extends substantially obliquely to the direction of movement of the sample therethrough.

10. The method according to claim 1, wherein the detection is performed by an array of detectors.

11. The method according to claim 1, wherein the electromagnetic radiation of a terahertz frequency has a frequency within the range from 100 GHz ($10^{11}$ Hz) to 30 THz ($3 \times 10^{13}$ Hz).

12. The method according to claim 1, wherein the products comprise pharmaceutical material.

13. The method according to claim 1, wherein the products comprise liquid material.

14. The method according to claim 1, wherein the products comprise powder material.

15. A conveyor system, comprising:
    means for filling a container with a product;
    means for conveying the container at a controlled velocity between functions of a production line and through an interrogation zone;
    means for generating at least one beam of electromagnetic radiation of a terahertz frequency;
    means for directing the beam through the interrogation zone;
    means for detecting the electromagnetic radiation reflected from or transmitted through the container as it moves through the interrogation zone;
    means for analyzing the detected electromagnetic radiation at least to determine physical or chemical characteristics of the product within the container; and
    means for outputting a signal to at least the filling means, wherein the signal corresponds to a result of analyzing the detected electromagnetic radiation.

16. The system according to claim 15, further comprising means for rejecting the container according to the result of analyzing the detected electromagnetic radiation.

17. A conveyor system, comprising:
    a filling station, configured to fill a container with a product;
    a conveyor configured to move the container at a controlled velocity from the filling station through an interrogation zone;
    a generator and transmitter system configured to generate at least one beam of electromagnetic radiation of a terahertz frequency and to direct the beam through the interrogation zone;
    a detector arranged on at least one side of the interrogation zone configured to detect the electromagnetic radiation reflected from or transmitted through the container and to analyze the detected radiation at least to determine physical or chemical characteristics of the product within the container,
    wherein the filling station is configured to receive a signal from the detector, wherein the signal corresponds to a result of analyzing the detected electromagnetic radiation.

18. The system according to claim 17, wherein a plurality of substantially parallel beams of electromagnetic radiation are directed through the interrogation zone.

19. The system according to claim 17, wherein the interrogation zone extends substantially orthogonally to the direction of movement of the container therethrough.

20. The system according to claim 17, wherein the interrogation zone extends substantially obliquely to the direction of movement of the container therethrough.

21. The system according to claim 17, wherein the detector comprises an array of detectors.

22. The system according to claim 17, wherein the electromagnetic radiation comprises a frequency within the range from 100 GHz ($10^{11}$ Hz) to 30 THz ($3 \times 10^{13}$ Hz).

23. The system according to claim 17, wherein the products comprise pharmaceutical material.

24. The system according to claim 17, wherein the products comprise liquid material.

25. The system according to claim 17, wherein the products comprise powder material.

* * * * *